(12) United States Patent
Crowe et al.

(10) Patent No.: US 8,494,658 B2
(45) Date of Patent: Jul. 23, 2013

(54) METHOD AND APPARATUS FOR STIMULATING PELVIC FLOOR MUSCLES

(75) Inventors: Louis Crowe, Dublin (IE); Brian Caulfield, Dublin (IE); Ruth Maher, Acworth, GA (US); Conor Minogue, Kinvara (IE)

(73) Assignees: University College Dublin, National University of Ireland, Dublin, Dublin (IE); Bio-Medical Research Limited, Galway (IE)

( * ) Notice: Subject to any disclaimer, the term of this patent is extended or adjusted under 35 U.S.C. 154(b) by 66 days.

(21) Appl. No.: 13/145,588

(22) PCT Filed: Jan. 8, 2010

(86) PCT No.: PCT/IB2010/000018
§ 371 (c)(1),
(2), (4) Date: Jul. 21, 2011

(87) PCT Pub. No.: WO2010/084391
PCT Pub. Date: Jul. 29, 2010

(65) Prior Publication Data
US 2011/0276108 A1    Nov. 10, 2011

(30) Foreign Application Priority Data

Jan. 26, 2009  (IE) .................................. S2009/0076

(51) Int. Cl.
*A61N 1/04*    (2006.01)
(52) U.S. Cl.
USPC ................. 607/138; 607/2; 607/149; 607/48; 607/49; 607/50; 607/51
(58) Field of Classification Search
USPC .................................. 607/48–51, 138, 2, 149
See application file for complete search history.

(56) References Cited

U.S. PATENT DOCUMENTS

| | | | |
|---|---|---|---|
| 3,610,250 A | | 10/1971 | Sarbacher |
| 5,702,428 A | * | 12/1997 | Tippey et al. ................... 607/41 |
| 5,871,534 A | * | 2/1999 | Messick et al. ............... 607/138 |
| 6,553,266 B1 | | 4/2003 | Yuang |
| 8,072,338 B2 | * | 12/2011 | Rondoni et al. ........... 340/573.5 |
| 2006/0247733 A1 | * | 11/2006 | Amer .............................. 607/48 |
| 2007/0049814 A1 | * | 3/2007 | Muccio ......................... 600/388 |
| 2007/0293911 A1 | * | 12/2007 | Crowe et al. .................... 607/48 |

* cited by examiner

*Primary Examiner* — Joseph Stoklosa
(74) *Attorney, Agent, or Firm* — Nath, Goldberg & Meyer; Jerald L. Meyer (57) ABSTRACT

A method of and apparatus for stimulating pelvic floor muscles in a patient comprises applying at least one electrode externally to each side of the patient's body in the region of the pelvis, and energising the electrodes to apply a muscular stimulation current which flows laterally across the patient through the patient's pelvic floor. Preferably a plurality of electrodes are applied symmetrically on each side of the body. The electrodes may be incorporated in a garment.

36 Claims, 8 Drawing Sheets

METHOD AND APPARATUS FOR STIMULATING PELVIC FLOOR MUSCLES

This is a National Phase Application filed under 35 U.S.C. 371 as a national stage of PCT/IB2010/000018, filed on 8 Jan. 2010, an application claiming the benefit from Irish Application No. S2009/0076, filed on 26 Jan. 2009, the entire content of each of which is hereby incorporated by reference in its entirety.

This invention relates to a method and apparatus for stimulating pelvic floor muscles in a patient, especially but not limited to stimulating such muscles to treat stress urinary incontinence.

BACKGROUND

Stress urinary incontinence (SUI) is a major medical problem that affects up to one third of middle aged women and has a significant impact on quality of life. A major contributing factor to the development of SUI is weakness and dysfunctional reflex activation of the muscles of the pelvic floor during times of increased bladder pressure. As with any muscle, these muscles will respond well to strengthening and re-education yet patients with SUI often find it very difficult to produce the effective voluntary contractions necessary for successful rehabilitation—due a combination of difficulty in establishing conscious control and disuse atrophy. There is a clear need for effective neuroprosthetic methodologies to facilitate effective pelvic floor contractions and promote successful rehabilitation for patients with SUI.

Previous research efforts have attempted to find effective means of using support mechanisms to facilitate pelvic floor contractions. One such method is the use of neuromuscular electrical stimulation (NMES)—a therapeutic approach that has been used in musculoskeletal rehabilitation for many years. NMES has been employed in the rehabilitation of SUI for some time now with generally positive, but mixed, results.

Since the early 1990s the most commonly used NMES method for incontinence rehabilitation is to use a vaginal or rectal electrode probe to deliver the electrical stimulation. By definition these probes are invasive and thus less appealing to many patients and clinicians. Patient comfort levels tend to be poor and the probe can also cause local tissue trauma with associated post treatment bleeding and tenderness. Whilst these invasive electrodes induce some pelvic floor contraction it is typically of limited strength; thus reducing its likely efficacy.

Current density around the area of the invasive electrode is high leading to an uncomfortable sensation for the patient, this is exacerbated by the tendency of the electrodes to fall away from the tissue. Further to this, the invasive electrodes can also cause minor tissue damage leading to further discomfort. This greatly limits the tolerance of NMES as a therapeutic approach for SUI and rehabilitation gains are often limited by poor compliance as a result.

In previous times NMES protocols for SUI were centred on use of pairs of relatively small electrodes situated over the belly and the muscle. Current flows from one to the other to produce a relatively simple electrical field in the area between the electrodes to produce the required pelvic floor contractions. However, the strength of contractions produced by these external electrode systems were generally poor and unpredictable and more recent approaches to using NMES in SUI treatment have employed an invasive approach.

There is therefore a need to develop an effective NMES treatment that avoid the need for invasive electrodes and relies instead on the use of external electrodes to produce a more acceptable and comfortable yet clinically effective treatment for SUI and other conditions.

SUMMARY OF THE INVENTION

According to the invention there is provided a method and apparatus for stimulating pelvic floor muscles in a patient, comprising applying at least one electrode externally to each side of the patient's body in the region of the pelvis, and energising the electrodes to apply a muscular stimulation current which flows laterally across the patient through the patient's pelvic floor.

The invention is based upon passing current across the pelvis from one leg/hip region to the other via the pelvic floor.

Acute effect ultrasound imaging studies have demonstrated very good recruitment of pelvic floor musculature using the invention, and have shown that this approach offers highly significant advantages over commercially available invasive electrode methods.

The method has also been tested to good effect in management of incontinence post hysterectomy and could have a role to play in management of fecal incontinence and urge incontinence.

Nonetheless, it is possible with the present method to add a sensor to detect pelvic floor activity. This could be a very small vaginal or anal EMG, pressure, or acceleration sensor.

In a second aspect of the invention there is provided an apparatus for stimulating pelvic floor muscles in a patient, comprising at least one electrode for application externally to each side of the patient's body in the region of the pelvis, and drive circuitry arranged to energise the electrodes to apply a muscular stimulation current which flows laterally across the patient through the patient's pelvic floor.

Preferably the electrodes are incorporated in a garment worn by the patient, the garment and electrodes being configured so that current flows laterally across the midline of the body.

BRIEF DESCRIPTION OF THE DRAWINGS

An embodiment of the invention will now be described, by way of example, with reference to the accompanying drawings, in which.

DESCRIPTION OF THE PREFERRED EMBODIMENT

Figure 1A:
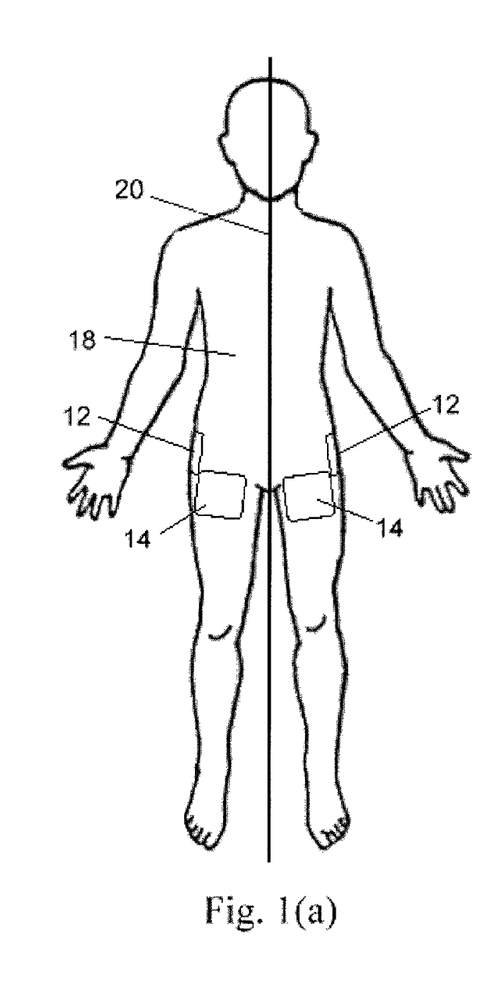
FIGS. 1(a), 1(b) and 1(c) are schematic views of, respectively, the front, back and right-hand side of a patient wearing a set of electrodes according to the embodiment.
Figure 1B:
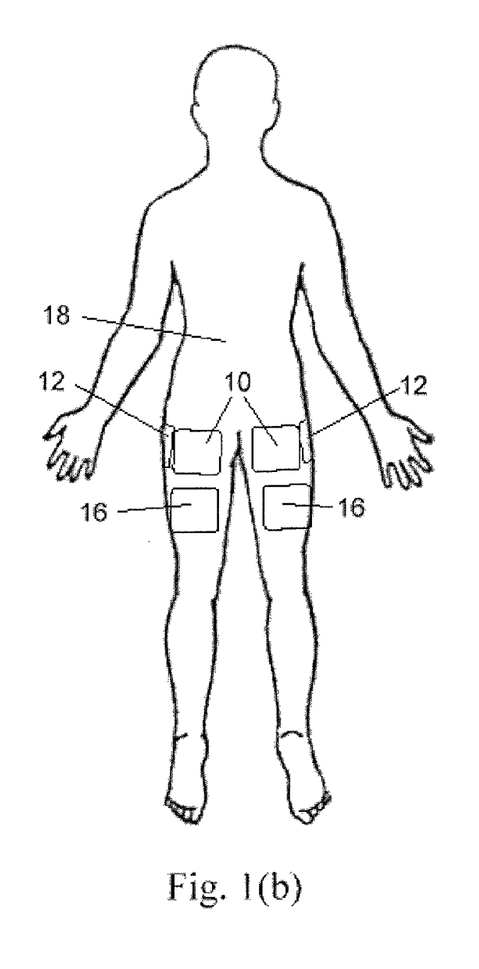
Figure 1C:
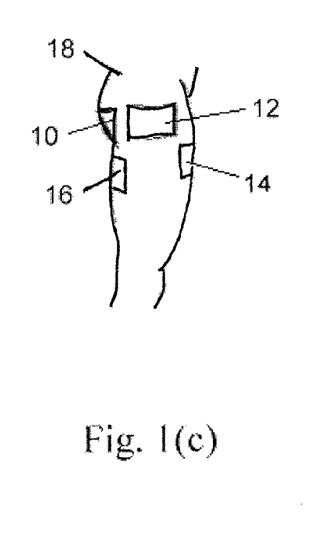

Referring to FIG. 1, in the embodiment a method of treating stress urinary incontinence in a patient comprises applying a respective set of large-area electrodes 10 to 16 externally to each side of the patient's body 18 in the region of the pelvis.

The two sets of electrodes are disposed on the patient's skin at least approximately symmetrically relative to the patient's midline 20. The electrodes comprise, on each side of the body 18, a first electrode 10 on the posterior pelvic, close to the mid-line cleft, centred near or below the point of maximum convexity, a second electrode 12 on the hip approximately horizontally in line with the electrode 10, a third electrode 14 on the upper front thigh, and a fourth electrode 16 on the upper back thigh. As used herein, expressions of orientation such as "vertical" and "horizontal" refer to the patient when standing. Contact wires (not shown) are connected individually to the electrodes which allow a muscular stimulation current to be applied to the patient, as will be described.

In this embodiment each electrode measures approximately 16×12 cm, giving a total area of electrodes on each side of the body of approximately 768 cm$^2$. The electrodes 10 to 16 are orientated with their major axes approximately horizontally on the body 18.

In general there may be fewer, or more, than four electrodes on each side of the body, but in all cases they should be located so that when the electrodes are energised a muscular stimulation current flows laterally across the patient through the patient's pelvic floor. We have found that the total area of the electrode(s) on each side of the body is preferably at least about 500 cm$^2$ in order to achieve strong and predominant pelvic floor contractions. Less electrode area can lead to localised contractions under the electrodes that limit the stimulation intensities and thus the stimulation of the pelvic floor. The optimal electrode pad area has been found to be 768 cm$^2$ per side of the body, as used in the present embodiment. With this arrangement the electrical impulses pass through the pelvis stimulating the pelvic nerves.

However many electrodes are used, we have found that it is advantageous for the electrodes, when in position on the body, to aggregately subtend a large arc in the horizontal plane with respect to the perineum. This ensures that the perineum is effectively encircled and so the field pattern of current flux diverges as much as possible.

Ideally, the electrodes on each side of the body would subtend an angle of at least 90°, and preferably 120°, with respect to the perineum.

This arrangement is a significant departure from current approaches to using NMES technology in rehabilitation.

When applied to the pelvic region as described, the electrodes are energised to apply a pulsed muscular stimulation current which flows laterally across the patient through the patient's pelvic floor in order to produce strong pelvic floor contractions. In the present context "laterally" means from side-to-side across the midline 20 of the patient's body.

Although the electrodes may be attached at their desired positions individually to the patient's skin, e.g. using hydrogel, it is preferred that they are incorporated in a garment which locates the electrodes more reliably at the desired positions.

Figure 2:
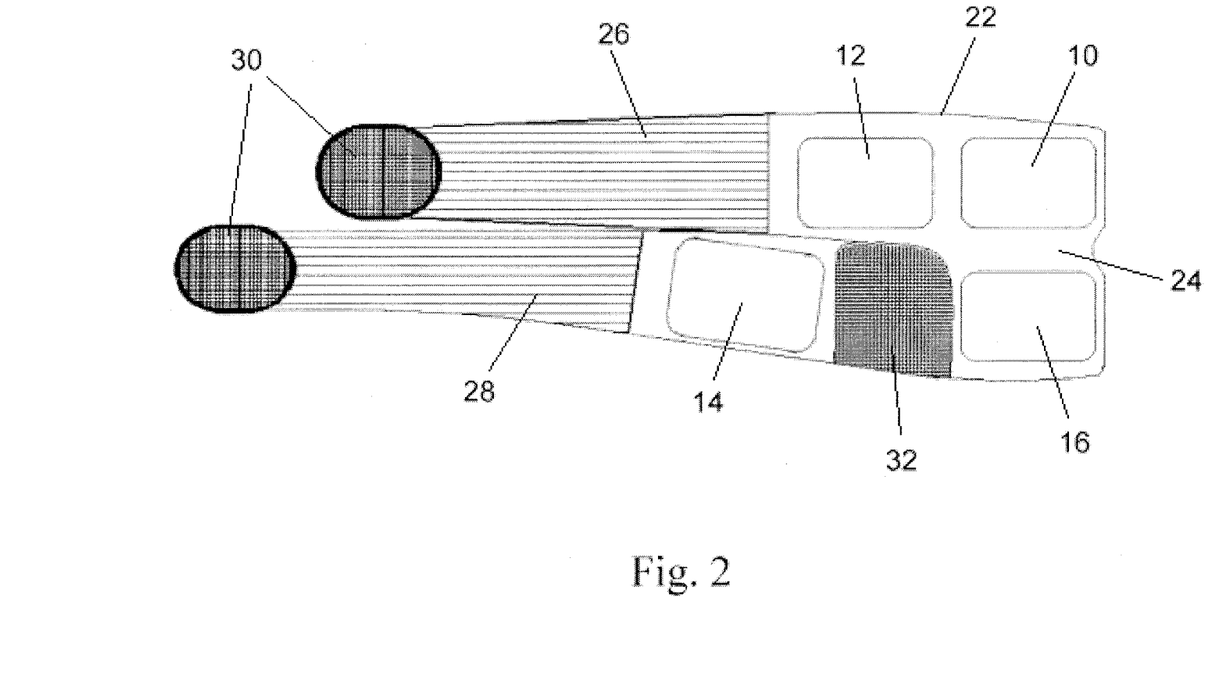
FIG. 2 is a plan view of the right-hand side part of a two-part garment incorporating the electrodes of FIG. 1.

An example is shown in FIG. 2, which is a plan view of the inside surface of the right-hand side part 22 of a two-part garment. The left-hand side part of the garment is substantially a minor image of the right-hand side part, and is therefore not shown.

The part 22, referred to herein as a wrap, incorporates the right-hand set of electrodes of FIG. 1. The wrap 22 comprises a main electrode-bearing portion 24 having two lateral finger-like extensions (straps) 26, 28 extending from one edge of the portion 24 and disposed one immediately above the other. In use the wrap 22 is wrapped around the patient's hip and thigh region with the electrodes on the inside, so that the electrodes 10 to 16 bear against the patient's skin at the appropriate locations on the patient's body. The straps 26, 28 are elasticated so that the wrap is stretched around the region for snug fitting. The wrap 22 is secured in place by Velcro hooks 30 at the free ends of the straps which engage a region of Velcro loops (not shown) on the outer surface of the electrode-bearing portion 24. Where the straps 26, 28 meet, that portion 24 of the wrap may be pleated to further facilitate the snug fitting of the wrap. The electrode-bearing portion 24 may also have an elasticated region 32 between the electrodes 14 and 16, to enhance the stretchability of the portion 24 in that area. Having areas of differing stretchability allows for a better fit.

The wrap 22 is fitted by first positioning the electrodes 10 and 16 at the appropriate locations on the rear of the pelvic region on the right side of the body, and then bringing the straps 26, 28 round to the front of the right thigh, threading them between the legs, and finally fixing their free ends to the portion 24 using the Velcro hooks 30. The left-hand side wrap, which is substantially a mirror-image of the right-hand side wrap 22, is fitted to the left hand side of the body in a similar way.

To reduce the number of wrap sizes required, the printing of the electrode positions may be different for small/medium/large body sizes. Electrodes 10 and 16 are positioned in relation to the mid-line and so do not differ greatly, regardless of subject size. A large subject would position electrodes 12 and 14 further outward on the wrap.

The material of the main electrode-bearing portion 24 of the wrap 22 may be a material that is resiliently deformable, such as neoprene, although less elastic than the straps 26, 28. To avoid separation of the electrodes from the portion 24 when the wrap is stretched around a subject, the latter may an inelastic material in the electrode regions.

Wiring (not shown) to the electrodes is integrated into the wrap 22; techniques are known to do this. The electrodes may be pre-fixed to the wrap at manufacture, or they may be fixed by the user at pre-printed locations on the portion 24. In the latter case the wiring for each electrode may terminate in an exposed stud in the centre of the electrode area. Adhesive electrodes are then placed onto the wrap in the designated areas. One side of the electrode sticks to the inner surface of the wrap and the other bears against the skin when the wrap is worn. The wiring allows each electrode to be individually energised if desired.

Figure 3:
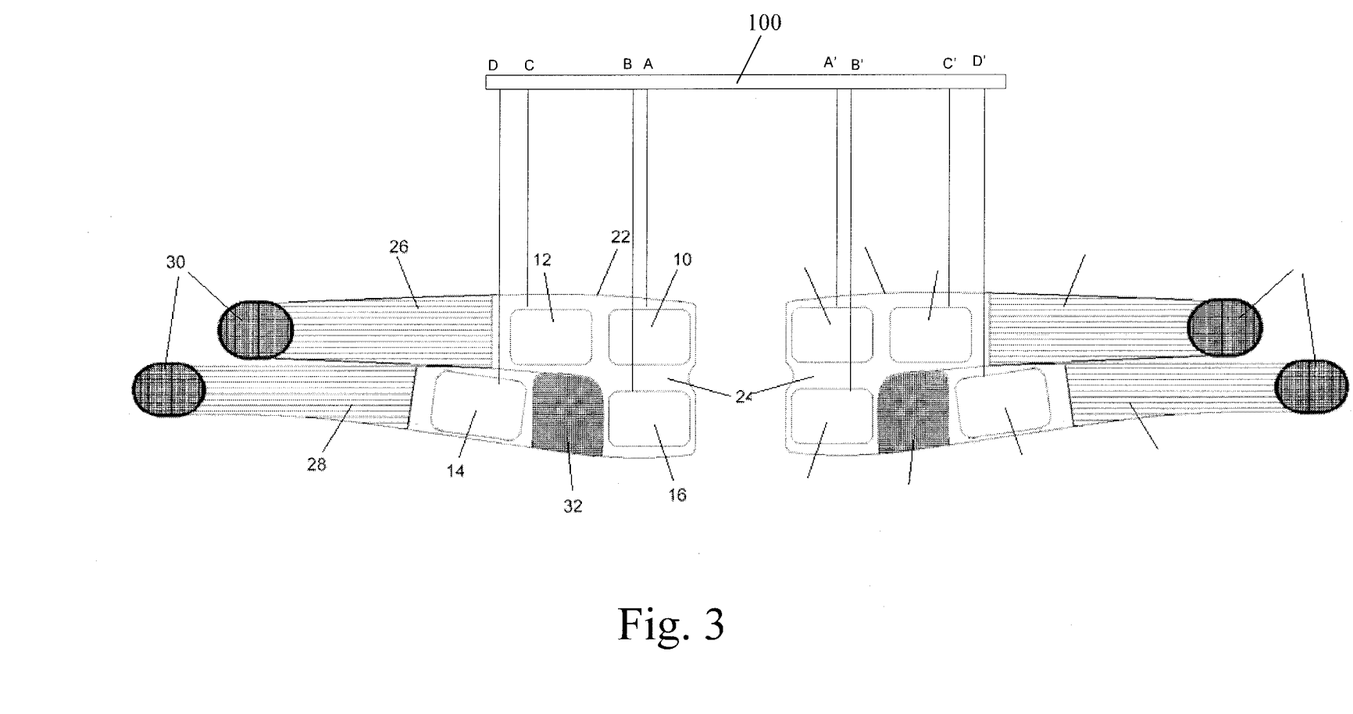
FIG. 3 is an example of a wiring arrangement for the garment of FIG. 2.

FIG. 3 is an example of the electrode wiring for the two-part garment of FIG. 2. FIG. 3 shows the complete garment comprising both the right- and left-hand side wraps. The drive circuitry 100 is also schematically illustrated and this may be constructed according to principles well-known in the NMES field.

The electrodes 10, 12, 14 and 16 of the right-hand side wrap are connected individually to respective driver nodes A, C, D and B, and the corresponding electrodes of the left-hand side wrap are connected to respective driver nodes A', C', D' and B'. Each driver node can be programmed to act, independently of the others, as a current source or a current sink, or to remain at high impedance. Under control of a microprocessor, each electrode may therefore be selected as a current source, a current sink or may be de-selected and take no part in the delivery of current. In this way electrodes may be combined into sets; a set with one polarity, a set with the opposite polarity, and a set not conducting at all. This allows for current to be directed between the eight electrodes of the garment via every possible pathway.

Importantly, each electrode has a defined anatomical position and is connected through the garment wiring and connectors to a particular driving node in the drive circuitry. Therefore, a current pathway established between nodes has a defined anatomical pathway, for example across the midline of the body. In a pre-wired garment these connections cannot be changed by the user so the intended anatomical pathways for the current cannot be changed by the user.

In the case shown in FIG. 3 where the garment is in two parts, one part for the left and one for the right, it is essential that each garment part is connected to the drive circuitry such that the intended anatomical relationship is preserved. This is readily achieved by keyed and/or polarised connectors which ensure that the garment connections cannot be swapped or mixed up.

In the simplest embodiment, the electrodes on one side of the body are selected as one polarity, and the electrodes on the other side are selected for the opposite polarity. In such a case individual energisation of the electrodes is not required, and therefore on each side of the body the electrodes may simply be connected together electrically within the garment and a single conductor brought to the drive circuitry. For example, the right-hand side electrodes 10, 12, 14 and 16 could be electrically connected together to form one large area multi-segment electrode on the right, and the corresponding left-hand side electrodes could be electrically connected together to form one large area multi-segment electrode on the left.

Whilst a two-part garment with a wrap for each leg is shown in FIGS. 2 and 3, other embodiments have been found to have advantages.

Figure 4:
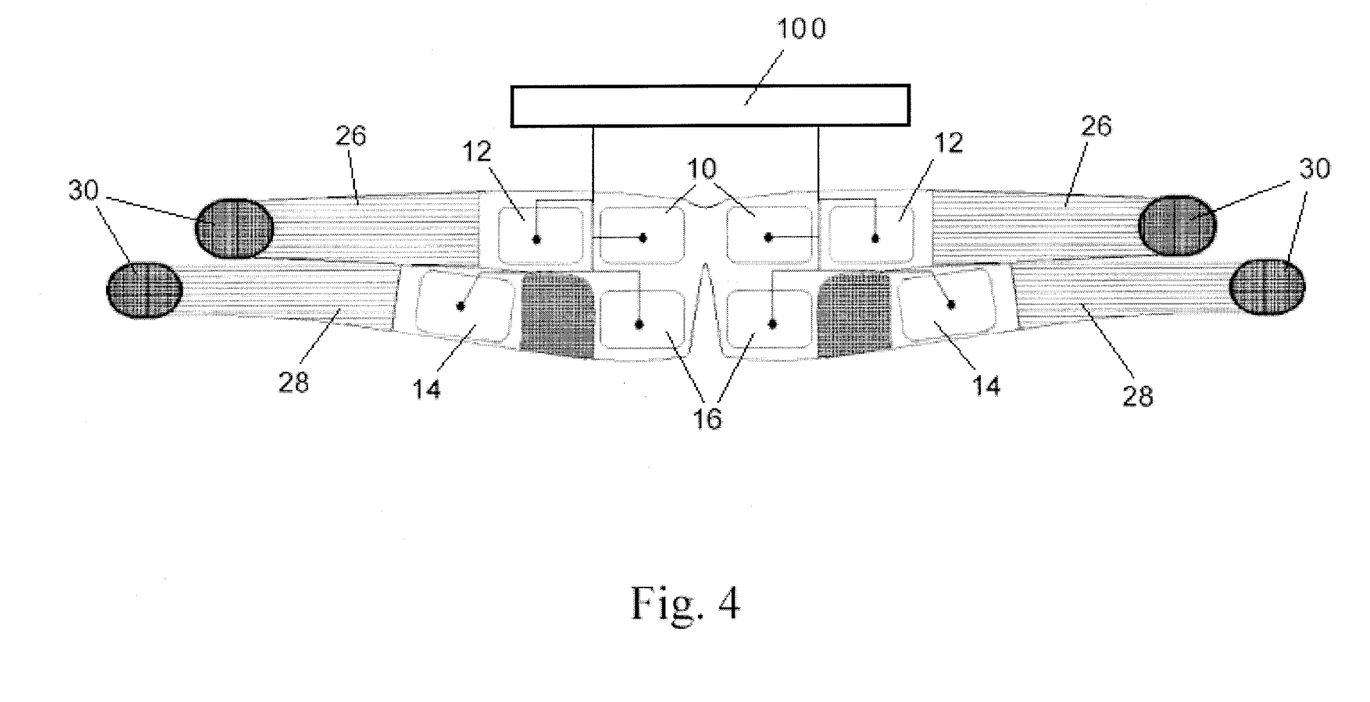
FIG. 4 is a modification of the embodiment of FIGS. 2 and 3.

For example, at least the upper parts of the inner edges of the electrode-bearing portions 24 of the right- and left-hand side wraps forming the garment of FIGS. 2 and 3 may be joined together to form a one-piece garment, as shown in FIG. 4. In fitting the garment the user may simply place the gluteal electrodes 10 first and then close the wrap as in the single leg version. Partially spitting the two sides of the garment (i.e. forming the separate straps 26, 28) has been found to ease its application.

The wiring may be integrated into the garment, as previously discussed. In FIG. 4 the four electrodes 10-16 on each side of the garment are shown connected in common to the drive circuitry 100. However, the electrodes may be individually connected, in the manner shown in FIG. 3. Also, since there is material continuity across both sides of the garment all the wiring may come out bundled at a single point for easy insertion into the drive circuitry. In this and all embodiments the drive circuitry 100 may be incorporated into the garment itself In two-part embodiments that have a separate garment part for each side of the body the wiring on one side of the body may connect directly to the drive circuitry or it may be connected to the drive circuitry via the other part of the garment.

It will be evident that the shape of the garment may be slightly modified so that it more closely resembles a typical disposable diaper or nappy, with flaps. The user may then position the garment as you would a nappy and close it using fasteners. The garment itself may also be made of disposable material (or at least a part of it).

Instead of a two-piece garment as described, both sets of electrodes could be incorporated on the inside surface of a one-part garment, such as a wrap-around skirt with a Velcro or buckle fixing, or a pair of, preferably elasticated, shorts.

Figure 5:
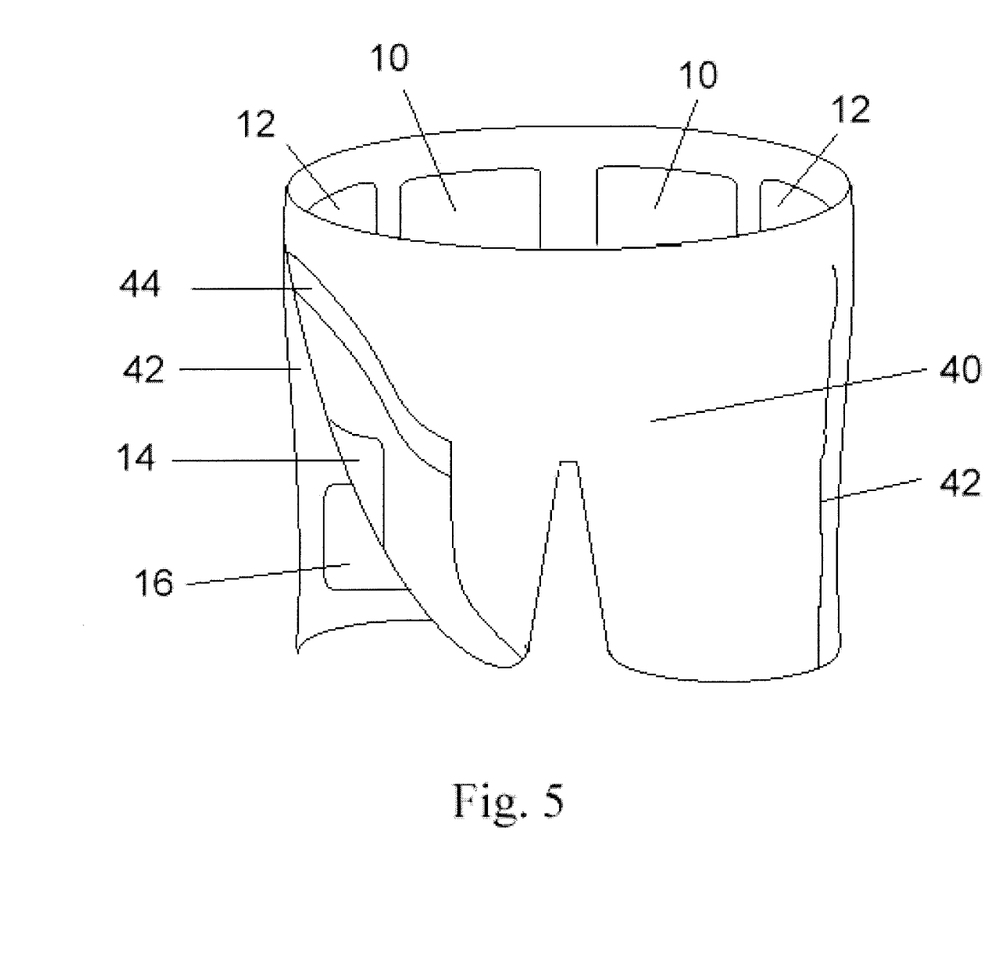
FIG. 5 shows an embodiment of the invention in the form of a pair of shorts incorporating the electrodes of FIG. 1.

FIG. 5 shows a pair of shorts 40 embodying the invention. In this case the electrodes 10-16 are provided on the inside surface of the shorts so that they are appropriately positioned against the skin when the shorts are worn (for clarity the wiring to the electrodes is not shown). When used in conjunction with adhesive gel electrodes or any electrode that may cause shearing on the skin it is advantageous to have the shorts loose when initially applying the garment, and then tightening it to bring the electrodes to bear against the skin in the correct position. This may be facilitated by providing closable slits 42 in the material of the shorts. Advantageously these slits may extend up either side of the shorts.

The opposite edges of the slits 42 may be fastened together after the garment is applied using a standard mechanism such as a strip of Velcro 44. When the material of the shorts is partially or fully elastic this has the further advantage of pressing the electrodes against the skin, improving connectivity. The shorts may incorporate the wiring to the electrodes. The direction of the wiring will depend on the position of the slits and whether they extend fully to the garment edges. In the embodiment shown the slits 42 extend up the side of the leg, but other arrangements are possible providing the slit(s) are appropriately placed to avoid interfering with the electrodes.

Another mechanism which has been found to be very advantageous in positioning the electrodes is the use of flaps (i.e. overlapping areas of material) on the garment. A flap may carry both an electrode and a wiring connection to that electrode, and in use is tucked under the outer material of the garment to bring the electrode directly against the skin. Placing an electrode on a flap which is tucked under the outer material of the garment frees the electrode from the outer garment, allowing more even compression Importantly, the outer garment may have a slit going over the electrode area without interfering with the electrode itself.

The flaps have also been found to be particularly helpful in allowing users to position the electrodes while wearing standard underwear. There is a tendency for underwear to cover some of the electrode. This is particularly frequent in the outer and upper-outer portion of the gluteal electrode (electrode 10). A flap allows for the underwear to be positioned between the flap and the main garment without the need to reposition (e.g. uncomfortably hitch up) the underwear.

When using electrodes that may be easily pulled over the skin, e.g. silicone rubber electrodes, it is not necessary that the garment be applied loose and tightened after. Extra compression of the electrodes against the skin may given by external straps, the intrinsic elasticity of the material or compressive techniques such as are used in the underwear industry, particularly those garments designed to shape/contour/compress the body. It will be evident that areas of differential stretch will be advantageous as indeed the use of flaps and tabs, etc.

Figure 6A:
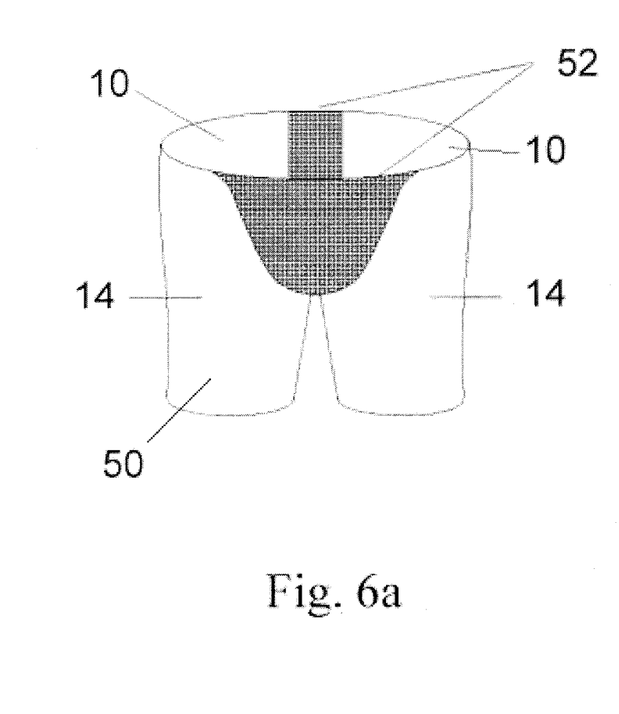
FIGS. 6a and 6b are front and back views respectively of a further pair of shorts embodying the invention.
Figure 6B:
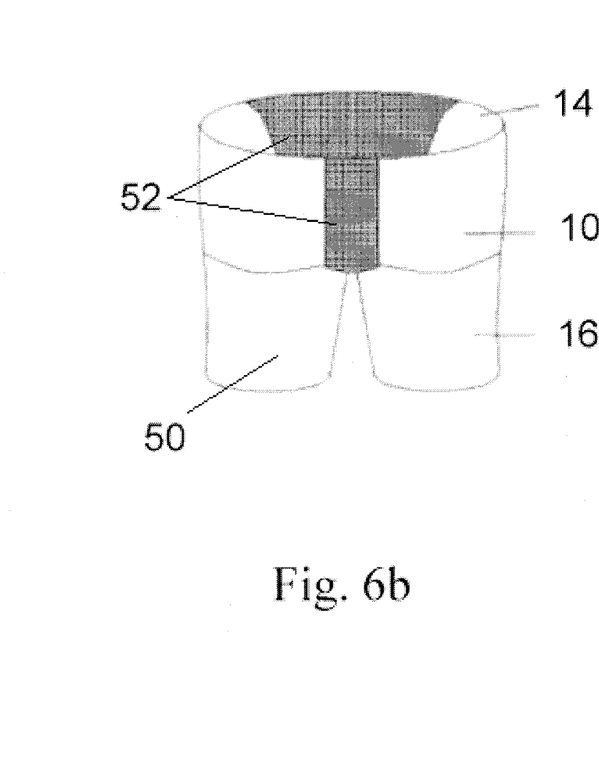

An example in the form of shorts 50 is shown in FIGS. 6a and 6b. The shorts themselves may be made of a conductive material or have conductive parts applied to it, e.g. a conductive fabric. Some areas 52 may be masked from skin contact to avoid unwanted stimulation, e.g. cutaneous stimulation of the perineum/scrotum/anal region. Alternatively, these areas may simply be made with non-conductive material. There may be slits or areas of non-conductive material between some or all of the electrode areas. This helps keep the electrodes discrete and ensures that the current passes deep within the tissue rather than passing along the surface between adjacent electrodes. Preferably the electrodes on each side of the body are separated from one another by at least a centimetre of non-conductive material for optimal stimulation. In FIG. 6 the electrodes on each side of the midline are not shown with a non-conducting area between them, because in some embodiments the left side acts as essentially one electrode and the right as another. It should be noted that this type of arrangement allows for an even greater surface area, and compensates for the inferior quality of connectivity typical for this type of fabric electrode.

For clarity the wiring of the shorts has not been shown. The shorts may be single layered or may have an external layer which is non-conductive, serving to further insulate the electrodes from touch from the outside. The external layer may add additional compression to the garment, and/or may carry conductors or electrical contacts to distribute current to the internal layer which may be positioned first.

In operation, the drive circuitry for the electrodes delivers biphasic current pulses, i.e. the current comprises alternate first and second phases in which every second phase pulse is inverted relative to the immediately preceding first phase pulse. It is not necessary that each second phase pulse have the same duration as the first phase pulse, but it preferably has the same total charge.

In order to reliably achieve significant pelvic floor contractions we found that a pulse current amplitude of at least about 80 mA was required, distributed over the four electrodes 10 to 16. Typically 80 mA is initially used and is then increased to 140 mA during the session. In subsequent sessions higher pulse currents may be used, but preferably not exceeding 200 mA.

Figure 7:
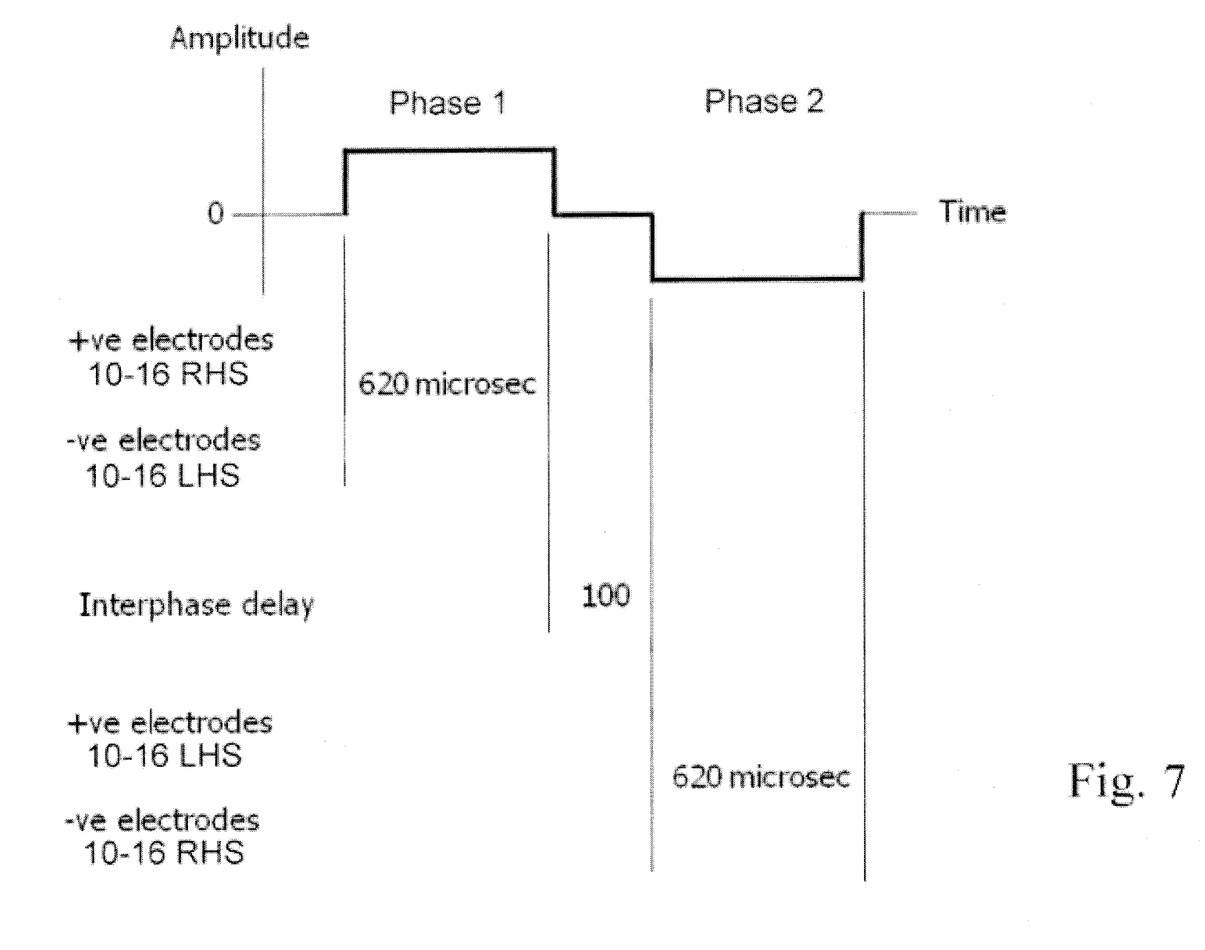
FIGS. 7 and 8 are timing diagrams showing examples of therapy using the electrodes of the preceding embodiments.

In a typical treatment session, FIG. 7, the overall duration of each first phase pulse is 620 microseconds, followed by an interphase delay of 100 microseconds when no current flows. Each second phase pulse is also 620 microseconds, but of opposite (negative) polarity.

The large electrode size allows the current density to remain tolerable going through the legs/hips/gluteal muscles. However it concentrates in crossing the pelvis, contracting the pelvic floor. For a peak current pulse amplitude of 80 mA, distributed over the area of the four pads on each side of the pelvic region, the peak current density at each electrode is:

$$80 \text{ mA}/768 \text{ cm}^2 = 0.1 \text{ mA/cm}^2$$

We have found that a simple pulse technique works well in most people, giving a strong pelvic floor contraction that can be readily tolerated. By a "simple pulse technique" we mean that the current pulses pass simultaneously from all the electrodes on the right to those on the left, and vice versa, according to the phase. Each set of electrodes 10 to 16 on each side of the pelvic region therefore acts as a single, multi-part electrode. FIG. 7 is an example of a simple pulse technique.

However, we have found that the pelvic floor contractions are further enhanced in some individuals if the current is passed selectively between one or more electrodes on one side to one or more electrodes on the other side, either during every current phase or in selected current phases, or portions of a phase.

Figure 8:
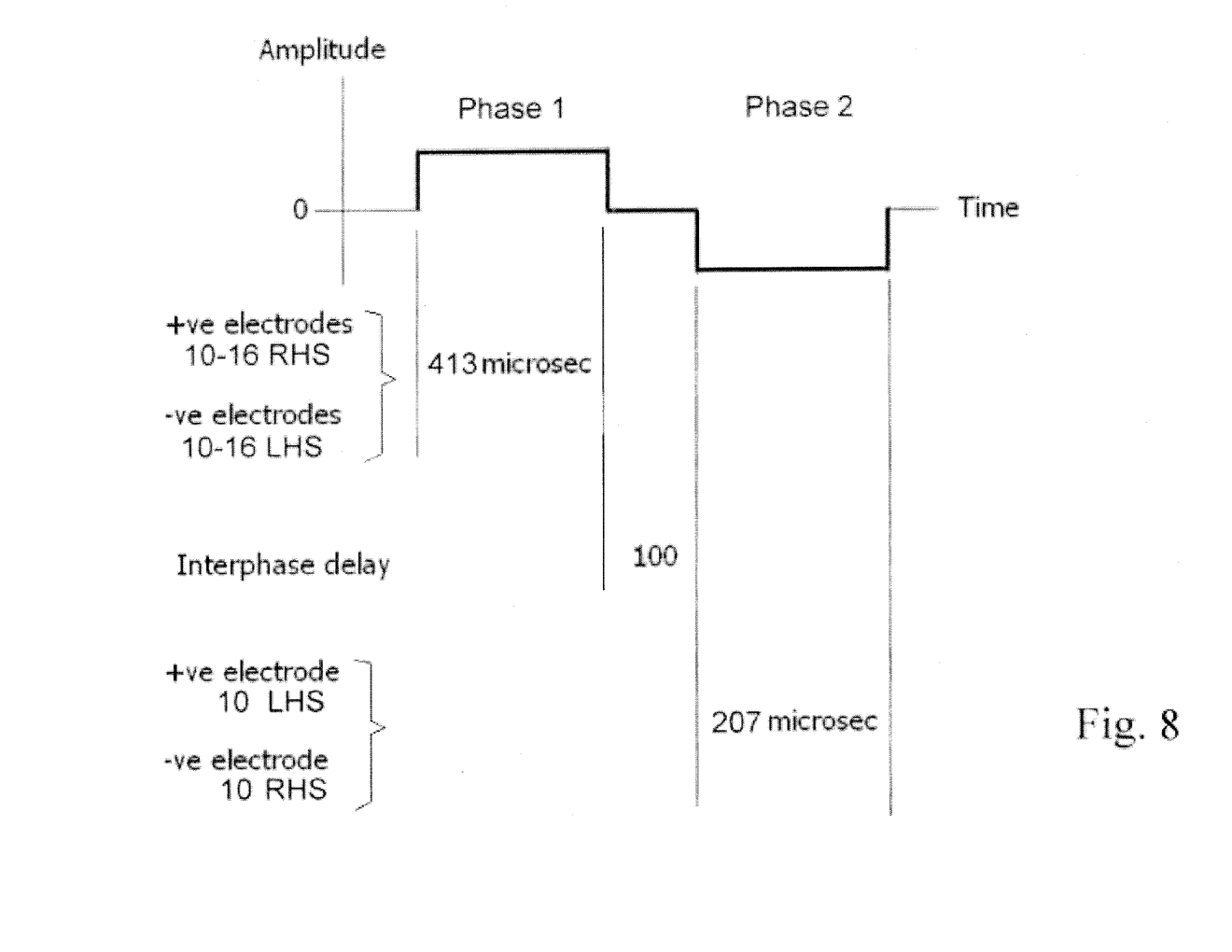

In a preferred embodiment, FIG. 8, each first phase is divided into two sub-phases, each first sub-phase current pulse has a duration of 413 microseconds and passes from all four electrodes on one side of the body to all four electrodes on the other side. Each second sub-phase current pulse has a duration of 207 microseconds but passes only between electrode 10 on one side to electrode 10 on the other side. The reverse polarity second phase follows the same pattern with current passing in the opposite direction between the same electrodes at the corresponding sub-phases. The sequence is as follows:

First Phase
First sub-phase: 413 microsecond pulse from all four electrodes on one side to all four electrodes on the other side.
Second sub-phase: 207 microsecond pulse from electrodes 10 and 12 on one side to the same electrodes on the other side.
Interphase interval 100 microsecond
Second Phase
First sub-phase: 413 microsecond pulse from all four electrodes on one side to all four electrodes on the other side.
Second sub-phase: 207 microsecond pulse from electrodes 10 and 12 on one side to the same electrodes on the other side.

The embodiments use relatively large currents, typically with peak pulse currents up to 200 mA and rms currents up to 50 mA. The charge per pulse phase can range from 40 up to 120 microcoulombs, compared to typical electrotherapy pulses which are usually limited in the region of 30 microcoulombs. These large currents and phase charges are tolerable only if they are dispersed over very large surface area electrodes. It is important therefore, for safety and comfort, that the apparatus can detect when the electrode surface area is reduced or if there is an increase in contact resistance with the skin.

While electrode impedance is related to surface area, the relationship varies with skin type, hair, amount of subcutaneous fat, cleanliness of the skin and condition of the electrodes. Therefore, impedance alone is not a reliable indicator of electrode surface area. Non-uniform impedance over the available surface area will lead to "hot spots" of current density at those points where the impedance is lowest. This problem may be overcome by passing test currents between the electrodes to compare one electrode impedance with others. In this way it is possible to establish if one electrode has an unexpectedly high, or low, circuit impedance which would lead to an imbalance of current density in the electrode array. Since, in the case where the electrodes are individually selectable, each electrode can be paired with any other electrode it is possible by a simple process of elimination to find the electrode, or electrodes, which are outliers in terms of electrical impedance. Having identified the electrode, the user can be alerted to take corrective action.

Accordingly, the circuitry includes means to determine the impedance of each electrode by measuring the voltage drop across each electrode due to a known test current, and an algorithm which analyses and compares the readings for each electrode. Pre-defined acceptance criteria for each electrode can be used to determine a fault condition, for example if there is a significant impedance imbalance between corresponding electrodes on opposite sides of the body. In addition, the electrode impedances so determined can be statistically analysed to identify outliers which fall outside a predefined range of the mean impedance of all the electrodes. The circuitry could also reject an electrode set if the statistical variance of the impedance values is higher than a preset amount.

The electrical impedance of an electrode in contact with the skin in the presence of an electrolyte is known to contain a large capacitative component which is due to the outer skin layer called the stratum corneum acting as a high impedance dielectric. The value of this capacitance increases with the area of contact. The impedance also has a parallel resistance component which decreases with area of contact. This resistive component also depends on the quality of the electrolyte. There is also a series resistance component which is primarily due to the internal resistance of the body. The quality of the electrolyte and its distribution, as well as presence of skin residues etc, also affects these impedance components.

The drive circuitry includes a means for measurement of electrode capacitance and estimation of the area of surface contact of each electrode, or any set of electrodes. The drive circuitry may be configured to signal a fault condition, and prevent the treatment beginning, or ceasing a treatment which is under way, when the estimated area of contact is below a pre-defined threshold, or lower by a pre-defined amount than an electrode of the same size elsewhere in the array.

The measurement of capacitance may be carried out by various techniques well known in electronic engineering. In a pulsed electrical stimulator it is convenient to take time domain measurements of voltage changes due to constant current test pulses in the microsecond range. By sampling the voltage across a pair of electrodes at several pre-defined time points in the charge and/or discharge phases of the pulse, it is possible to estimate charge and/or discharge time constants and therefore estimate each, or some, of the components in the model, i.e. the series resistance component, the parallel resistance component and the capacitance.

The current paths may change somewhat depending on the alignment of the pelvis, etc. Optimal stimulation of the pelvic floor is more likely with the subject in particular positions/ postures. In particular there appears to be a benefit in having the patient standing. This also has the advantage of being more 'physiological', i.e. for mechanical reasons stress incontinence often happens when the person is upright. The weight of the abdominal contents place extra pressure on the pelvic floor. Exercising the muscles in this position replicates what the muscles must do in reality. Intra-vaginal probe electrodes are usually used lying/sitting as otherwise the electrode has a tendency to fall making the contact with the target tissue poor and hence more uncomfortable.

Further observations include that the wearing of high-heels can disimprove the pelvic floor contractions. Additionally, the posture that typically gives the best contraction is standing with the feet apart and the subject leaning forward slightly with their hands on a ledge or table near hip height.

In trials, some women have, surprisingly, noticed an immediate effect upon using this type of stimulation. These effects are too sudden and quick to be accounted for by "training" of the muscles. Instead a re-awakening or activation of previously inhibited muscles or unused muscle is a possibility or an education/biofeedback in what contraction of these muscle fibres feels like.

This falls into two categories. Firstly, some women learn how to contract the pelvic floor that were previously unable to do so even under expert guidance with the assistance of ultrasound.

The inability of many women to voluntarily contract these muscles means that exercises are not going to do any good. With just a session of this new electrical stimulation they were able to voluntarily contract their pelvic floor.

Secondly, some women, especially post-hysterectomy patients, who had been incontinent for years got a sudden and immediate improvement in their incontinence after just a session using the new device.

In addition to the categories already discussed, the invention may be used to treat vaginal prolapse in females. We found in one case that after only eight sessions of stimulation the prolapse had resolved. This is probably because training the pelvic floor improved the tissue that keeps the vagina in position. This represents an alternative treatment for this condition, which had often required surgery.

Furthermore some women reported enhanced sexual gratification after using the machine.

The invention is not limited to the embodiment described herein which may be modified or varied without departing from the scope of the invention.

The invention claimed is:

1. A method of stimulating pelvic floor muscles in a patient, comprising applying at least one electrode externally to each side of the patient's body in the region of the pelvis, said electrodes cumulatively making an area of conductive contact with the body surface which substantially encircles the perineum, said area of contact including, on each side of the body, at least a part of each of the gluteal region, the hip, the upper front thigh and the upper back thigh, and energising the electrodes to apply a muscular stimulation current which flows laterally across the patient through the patient's pelvic floor.

2. The method claimed in claim 1, wherein the electrodes are disposed at least approximately symmetrically relative to the patient's midline.

3. The method claimed in claim 1, wherein the total area of the electrode(s) on each side of the body is at least about 500 cm2.

4. The method claimed in claim 1, wherein there are a plurality of electrodes on each side of the body.

5. The method claimed in claim 4, wherein the plurality of electrodes comprises, on each side of the body, a first electrode over the gluteal region, a second electrode on the hip, a third electrode on the upper front thigh, and a fourth electrode on the upper back thigh.

6. The method claimed in claim 1, wherein the electrodes are incorporated in a garment which locates the electrodes at desired positions against the patient's skin.

7. The method claimed in claim 6, wherein the garment comprises two parts each of which is wrapped around a respective thigh of the patient, each part incorporating the electrode(s) on one side of the body.

8. The method claimed in claim 7, wherein each part comprises a main electrode-bearing portion having two lateral straps extending in the same direction from one edge of the main electrode-bearing portion and disposed one above the other.

9. The method claimed in claim 6, wherein the garment comprises one part incorporating the electrodes on both sides of the body.

10. The method claimed in claim 9, wherein the garment comprises a main electrode-bearing portion having a respective pair of lateral straps extending in opposite directions from opposite edges of the main electrode-bearing portion and disposed one above the other.

11. The method claimed in claim 9, wherein the garment comprises a pair of shorts.

12. The method claimed in claim 6, wherein the garment comprises at least one electrode-bearing flap which in use is tucked under an outer layer of material of the garment.

13. The method claimed in claim 6, wherein the garment comprises at least one closable slit.

14. The method claimed in claim 1, wherein the electrodes are energised with biphasic current pulses.

15. The method claimed in claim 14, wherein the electrodes are energised with a simple pulse technique.

16. The method claimed in claim 14, wherein the electrodes are energised by passing current selectively between one or more electrodes on one side of the patient's body to one or more electrodes on the other side, either during every current phase or in selected current phases.

17. The method claimed in claim 14, wherein during each current pulse the total charge per phase is greater than 50 microcoulombs.

18. An apparatus for stimulating pelvic floor muscles in a patient, comprising at least one electrode for application externally to each side of the patient's body in the region of the pelvis, said electrodes configured to cumulatively make an area of conductive contact with the body surface which substantially encircles the perineum, said area of contact including, on each side of the body, at least a part of each of the gluteal region, the hip, the upper front thigh and the upper back thigh, and drive circuitry arranged to energise the electrodes to apply a muscular stimulation current which flows laterally across the patient through the patient's pelvic floor.

19. The apparatus claimed in claim 18, wherein the electrodes are incorporated in a garment worn by the patient.

20. The apparatus claimed in claim 19, wherein the garment comprises two parts each of which is wrapped around a respective thigh of the patient, each part incorporating the electrode(s) on one side of the body.

21. The apparatus claimed in claim 20, wherein each part comprises a main electrode-bearing portion having two lateral straps extending in the same direction from one edge of the main electrode-bearing portion and disposed one above the other.

22. The apparatus claimed in claim 19, wherein the garment comprises one part incorporating the electrodes on both sides of the body.

23. The apparatus claimed in claim 22, wherein the garment comprises a main electrode-bearing portion having a respective pair of lateral straps extending in opposite directions from opposite edges of the main electrode-bearing portion and disposed one above the other.

24. The apparatus claimed in claim 22, wherein the garment comprises a pair of shorts.

25. The apparatus claimed in claim 19, wherein the garment comprises at least one electrode-bearing flap which in use is tucked under an outer layer of material of the garment.

26. The apparatus claimed in claim 19, wherein the garment comprises at least one closable slit.

27. The apparatus claimed in claim 19, wherein when the garment is worn the electrodes are disposed at least approximately symmetrically relative to the patient's midline.

28. The apparatus claimed in claim 18, wherein the total area of the electrode(s) on each side of the body is at least about 500 cm2.

29. The apparatus claimed in claim 18, wherein there are a plurality of electrodes on each side of the body.

30. The apparatus claimed in claim 29, wherein the plurality of electrodes comprises, on each side of the body, a first electrode over the gluteal region, a second electrode on the hip, a third electrode on the upper front thigh, and a fourth electrode on the upper back thigh.

31. The apparatus claimed in claim 18, wherein the drive circuitry energises the electrodes with biphasic current pulses.

32. The apparatus claimed in claim 31, wherein the drive circuitry energises the electrodes with a simple pulse technique.

33. The apparatus claimed in claim 31, wherein the drive circuitry energises the electrodes by passing current selectively between one or more electrodes on one side of the patient's body to one or more electrodes on the other side, either during every current phase or in selected current phases.

34. The apparatus claimed in claim 31, wherein during each current pulse the charge per phase is greater than 50 microcoulombs.

35. The apparatus claimed in claim 18, wherein said drive circuitry includes means for measuring the impedance of each electrode and signalling a fault condition if pre-defined acceptance criteria for each electrode are not met.

36. The apparatus claimed in claim 18, wherein said drive circuitry includes means for estimating the area of surface contact of each electrode, or any set of electrodes, and signalling a fault condition if the estimated area of contact is below a pre-defined threshold, or lower by a pre-defined amount than another electrode of the same size.

* * * * *